US010668205B2

(12) United States Patent
Guala

(10) Patent No.: US 10,668,205 B2
(45) Date of Patent: Jun. 2, 2020

(54) FLOW COMPONENT PARTICULARLY FOR HAEMODIALYSIS MEDICAL LINES

(71) Applicant: Industrie Borla S.p.A., Moncalieri, Turin (IT)

(72) Inventor: Gianni Guala, Turin (IT)

(73) Assignee: Industrie Borla S.p.A., Moncalieri, Turin (IT)

( * ) Notice: Subject to any disclaimer, the term of this patent is extended or adjusted under 35 U.S.C. 154(b) by 3 days.

(21) Appl. No.: 15/654,192

(22) Filed: Jul. 19, 2017

(65) Prior Publication Data

US 2018/0021502 A1    Jan. 25, 2018
US 2018/0133390 A9    May 17, 2018

(30) Foreign Application Priority Data

Jul. 19, 2016    (IT) .................. 102016000075597

(51) Int. Cl.
*A61M 1/36* (2006.01)
*A61M 39/10* (2006.01)
*A61M 39/02* (2006.01)
*A61M 39/26* (2006.01)
(Continued)

(52) U.S. Cl.
CPC ............ *A61M 1/367* (2013.01); *A61M 39/02* (2013.01); *A61M 39/045* (2013.01); *A61M 39/10* (2013.01); *A61M 39/105* (2013.01); *A61M 39/22* (2013.01); *A61M 39/223* (2013.01); *A61M 39/26* (2013.01); *A61M 2039/1083* (2013.01); *A61M 2039/1088* (2013.01); *A61M 2205/0216* (2013.01); *A61M 2206/12* (2013.01)

(58) Field of Classification Search
CPC .... A61M 39/225; A61M 39/04; A61M 39/10; A61M 39/26; A61M 39/105; A61M 39/045; A61M 39/1011; A61M 1/1601

USPC ......................................................... 604/48
See application file for complete search history.

(56) References Cited

U.S. PATENT DOCUMENTS

| 5,533,708 A * | 7/1996 | Atkinson | A61M 39/045 251/149.1 |
| 9,044,585 B2 * | 6/2015 | Masuda | A61M 39/045 |
| 9,541,227 B2 * | 1/2017 | Okiyama | A61M 39/045 |

(Continued)

FOREIGN PATENT DOCUMENTS

| EP | 1661599 B1 | 2/2008 |
| JP | 2006129884 A | 5/2006 |
| JP | 2006223587 A | 8/2006 |

OTHER PUBLICATIONS

Italian Search Report and Written Opinion for IT Application No. IT201600075597 dated May 16, 2017, 8 pages.

*Primary Examiner* — Bhisma Mehta
*Assistant Examiner* — Nidah M Hussain
(74) *Attorney, Agent, or Firm* — Heslin Rothenberg Farley & Mesiti P.C.; Victor A. Cardona, Esq.

(57) ABSTRACT

A flow component particularly for hemodialysis medical lines includes a duct having a first and a second end tubular connector coaxial to each other and designed to be connected to the line, and an intermediate tubular connector of the female luer type arranged orthogonally to the duct. A hollow elastic element substantially extends along the entire intermediate tubular connector and the body is internally configured so that, in use, the flow along the duct is partly diverted towards the intermediate tubular connector and introduced with a swirling motion along the cavity of the hollow elastic element.

7 Claims, 4 Drawing Sheets

(51) Int. Cl.
*A61M 39/22* (2006.01)
*A61M 39/04* (2006.01)

(56) References Cited

U.S. PATENT DOCUMENTS

| | | | | |
|---|---|---|---|---|
| 9,775,981 B2* | 10/2017 | Nelson | | A61M 39/225 |
| 9,884,177 B2* | 2/2018 | Ueda | | A61M 39/1011 |
| 2003/0153897 A1* | 8/2003 | Russo | | A61M 39/045 |
| | | | | 604/537 |
| 2007/0218745 A1* | 9/2007 | Yokota | | A61M 39/045 |
| | | | | 439/357 |
| 2008/0086097 A1* | 4/2008 | Rasmussen | | A61M 39/045 |
| | | | | 604/266 |
| 2010/0030194 A1* | 2/2010 | Yokota | | A61M 39/1011 |
| | | | | 604/535 |
| 2011/0060293 A1* | 3/2011 | Guala | | A61M 39/10 |
| | | | | 604/246 |
| 2011/0172609 A1* | 7/2011 | Moga | | A61M 5/14224 |
| | | | | 604/272 |
| 2013/0237923 A1* | 9/2013 | Ueda | | A61M 39/045 |
| | | | | 604/246 |
| 2014/0207117 A1* | 7/2014 | Ueda | | A61M 39/02 |
| | | | | 604/533 |
| 2014/0276215 A1* | 9/2014 | Nelson | | A61M 39/225 |
| | | | | 600/573 |
| 2014/0332091 A1* | 11/2014 | Ueda | | A61M 39/26 |
| | | | | 137/15.18 |
| 2015/0013807 A1* | 1/2015 | Ueda | | F16K 11/0873 |
| | | | | 137/625.47 |
| 2015/0112271 A1* | 4/2015 | Chelak | | A61M 39/06 |
| | | | | 604/186 |
| 2015/0190623 A1* | 7/2015 | Ueda | | A61M 39/045 |
| | | | | 604/537 |
| 2015/0297817 A1* | 10/2015 | Guala | | A61M 39/26 |
| | | | | 604/256 |
| 2015/0297880 A1* | 10/2015 | Ogawa | | A61M 39/045 |
| | | | | 604/247 |
| 2016/0022978 A1* | 1/2016 | Ueda | | A61M 39/105 |
| | | | | 604/250 |
| 2017/0120031 A1* | 5/2017 | Guala | | A61M 39/1011 |
| 2017/0368325 A1* | 12/2017 | Ueda | | A61M 5/14 |
| 2018/0015278 A1* | 1/2018 | Ueda | | A61M 39/10 |
| 2018/0021502 A1* | 1/2018 | Guala | | A61M 1/367 |
| | | | | 137/320 |
| 2018/0099135 A1* | 4/2018 | Hall | | A61M 39/10 |

* cited by examiner

FLOW COMPONENT PARTICULARLY FOR HAEMODIALYSIS MEDICAL LINES

CROSS REFERENCE TO RELATED APPLICATIONS

This application claims priority to Italian Application No. 102016000075597 filed on Jul. 19, 2016. The entire disclosure of the prior application is hereby incorporated herein by reference.

FIELD OF THE INVENTION

The present invention generally refers to liquid flow lines, particularly but not exclusively hemodialysis medical lines and more in particular it regards a flow component for lines thus made of the type comprising a body defining a duct having a first and a second end tubular connector coaxial to each other and designed to be connected to the line, and an intermediate tubular connector arranged orthogonally to the duct between said end connectors and containing a valve device.

STATE OF THE PRIOR ART

A flow component of the type defined above is for example known from document EP-1661599B1 on behalf of the Applicant, in which the valve device consists in a hollow elastic element which normally holds said intermediate tubular connector closed and it is elastically deformable following the coupling of the intermediate tubular connector with a complementary male luer connector to enable the introduction of a secondary liquid in the duct. The hollow elastic element consists in a simple diaphragm housed in a chamber comprised between the duct and the intermediate tubular connector of the body, and the chamber is in communication with a converging and diverging section of the duct through a pair of radial holes. With this arrangement, the intermediate tubular connector is difficult to clean before use and can thus be exposed to risks of contamination from the external environment.

Various valves of the so-called "swabbable" type, constituted by an elongated elastic body extending into a female luer lock connector up to the free end thereof, thus the end exposed towards the external of the elastic body can be easily cleaned and disinfected before the coupling of the female connector with a complementary male connector, are known in the prior art. An example of an elastic body thus made is described and illustrated in document U.S. Pat. No. 5,533,708.

It would be desirable to be able to use a similar elastic element in the flow component of the type defined at the beginning, so as to avoid risks of contaminating the intermediate tubular connector and benefiting from the "swabbable" characteristic of the elastic element. However, the axially extended inner cavity of the hollow elastic element according to U.S. Pat. No. 5,533,708 would entail, in particular in application to a hemodialysis medical lines, an extensive stagnation dead area and thus the deterioration of the blood, and this would be unacceptable.

Document US-2014/0207117 discloses a flow component of the type defined at the beginning in which the elastic body consists of a solid block that occupies only the free end area of the intermediate tubular connector. The flow component is configured so that the fluid flow along the duct is diverted towards the intermediate connector, so as to avoid stagnation in the area of the intermediate tubular connector located beneath the solid elastic body. This arrangement is disadvantageous due to the conformation and arrangement of the elastic body which also complicates the traversing thereof by a fluid introducer fitted into the intermediate tubular connector.

SUMMARY OF THE INVENTION

The object of the invention is to overcome the aforementioned technical drawback and enable, in a flow component of the type defined at the beginning, the use—in the relative intermediate tubular connector—of a hollow elastic element similar to the one mentioned in document U.S. Pat. No. 5,533,708.

According to the invention, this object is attained thanks to a flow component as defined in the pre-characterised part of claim 1, whose distinctive characteristic lies in the fact that the hollow elastic element substantially extends into the entire intermediate tubular connector and the body of the flow component is internally configured so that, in use, the liquid flow along the duct is partly diverted towards the intermediate tubular connector and introduced with a swirling motion along the cavity of said hollow elastic element.

Thanks to this solution idea, the flow component according to the invention is thus provided with an intermediate tubular connector efficiently protected by the hollow elastic element that can be cleaned from the external without any risk, in use, of liquid stagnation therein, in that the swirling flow generated in the cavity thereof generates a constant fluid change.

According to a preferred embodiment of the invention, the intermediate tubular connector is delimited, on the side of said duct, by a wall for supporting the hollow elastic element which is formed with two juxtaposed by-pass apertures, respectively upstream and downstream with respect to the flow in the duct, the by-pass apertures being shaped and oriented to generate the aforementioned swirling motion. To this effect, the two by-pass apertures are conveniently substantially semi-circular-shaped and they are oriented obliquely with respect to the axis of the duct.

Due to this configuration, the swirling motion of the liquid diverted towards the intermediate tubular connector and introduced along the cavity of said hollow elastic element, becomes particularly efficient.

BRIEF DESCRIPTION OF THE DRAWINGS

The invention will now be described in detail with reference to the attached drawings, provided purely by way of non-limiting example, wherein.

DETAILED DESCRIPTION OF THE INVENTION

Figure 1:
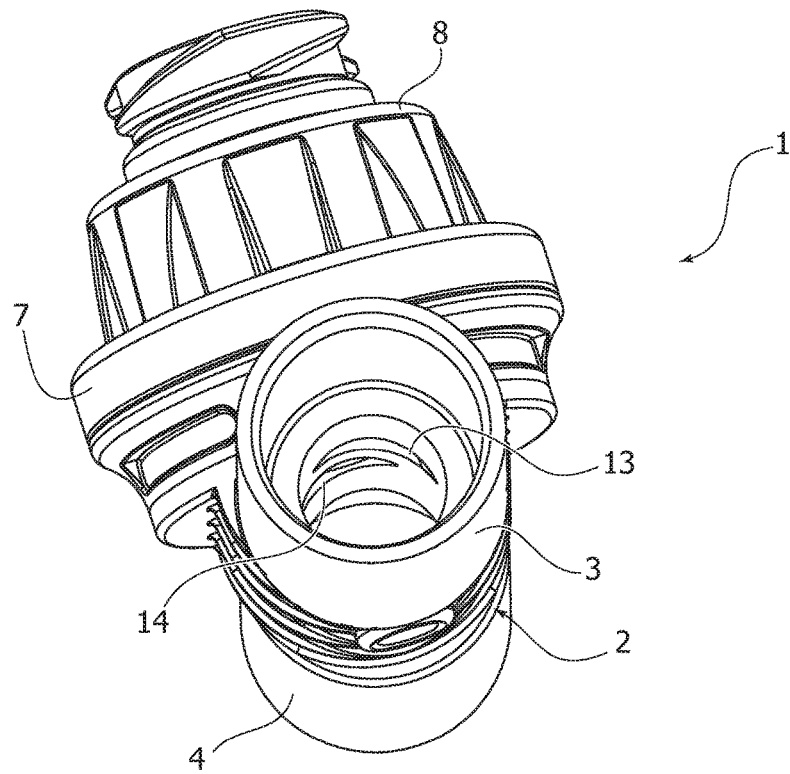
FIG. 1 is a schematic perspective view of a flow component for hemodialysis medical lines according to the invention.

The example represented in the drawings refers to the application of the invention to a hemodialysis medical line. However, it should be observed that the invention is equally advantageously applicable to any liquid flow line revealing the same technical drawback.

Figure 2:
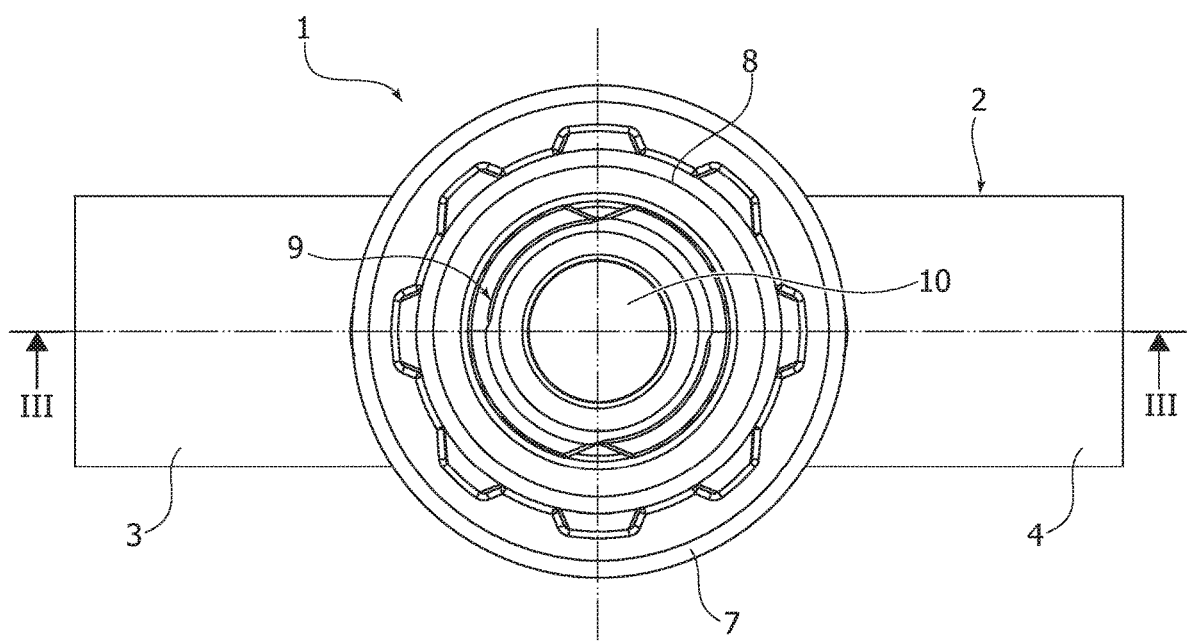
FIG. 2 is a top view of the flow component.
Figure 3:
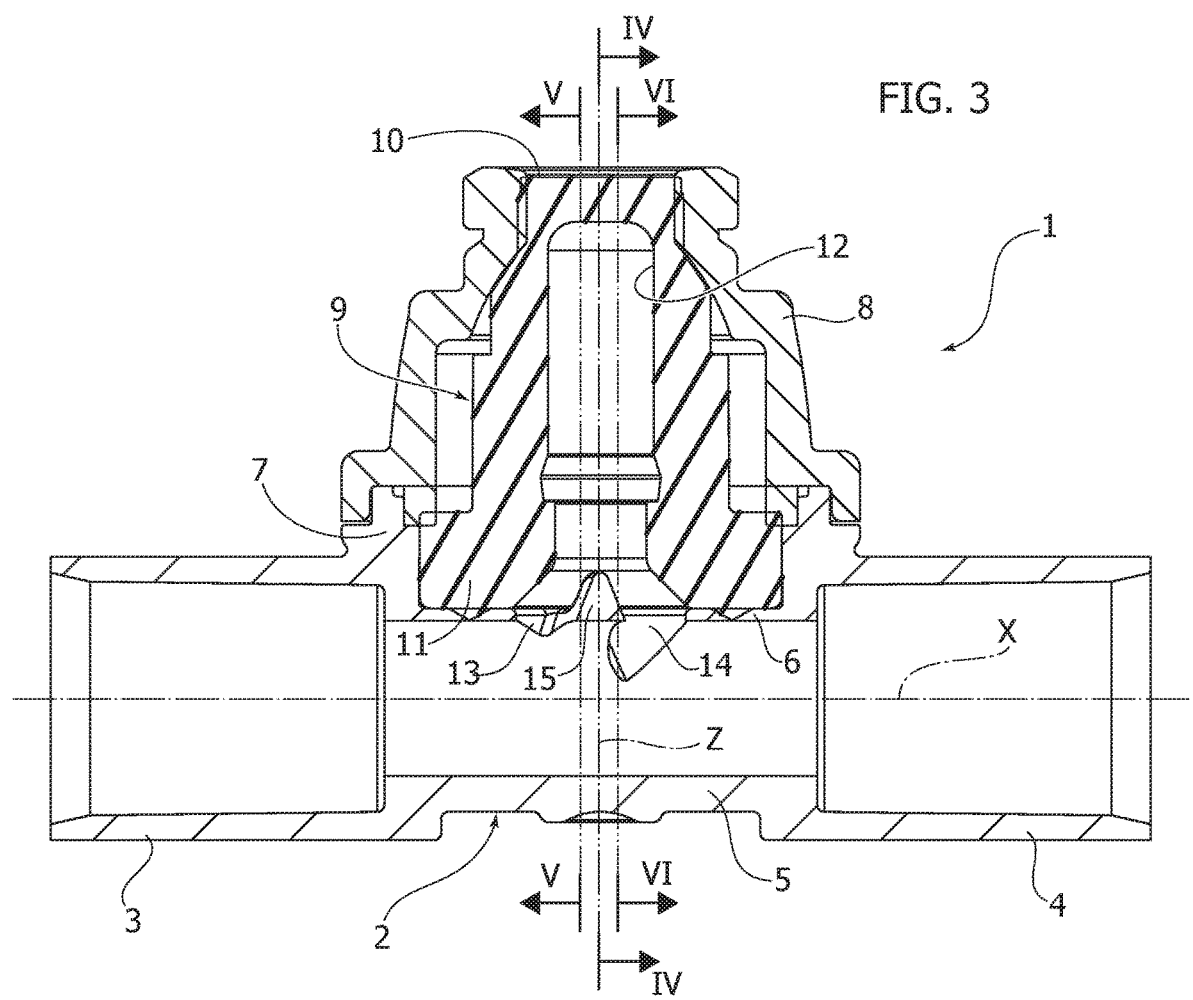
FIG. 3 is a longitudinal sectional view according to line of FIG. 2.
Figure 4:
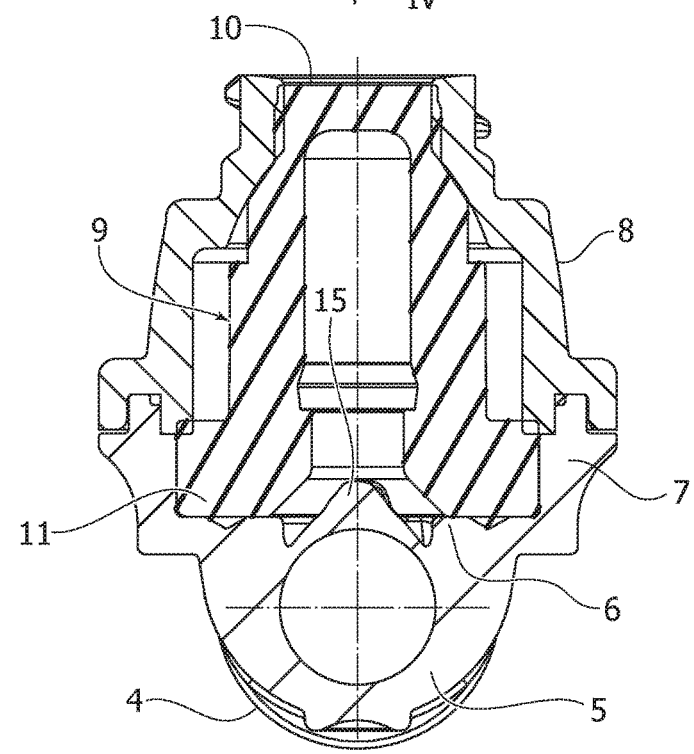
FIG. 4 is a cross-sectional view according to line IV-IV of FIG. 3.
Figure 5:
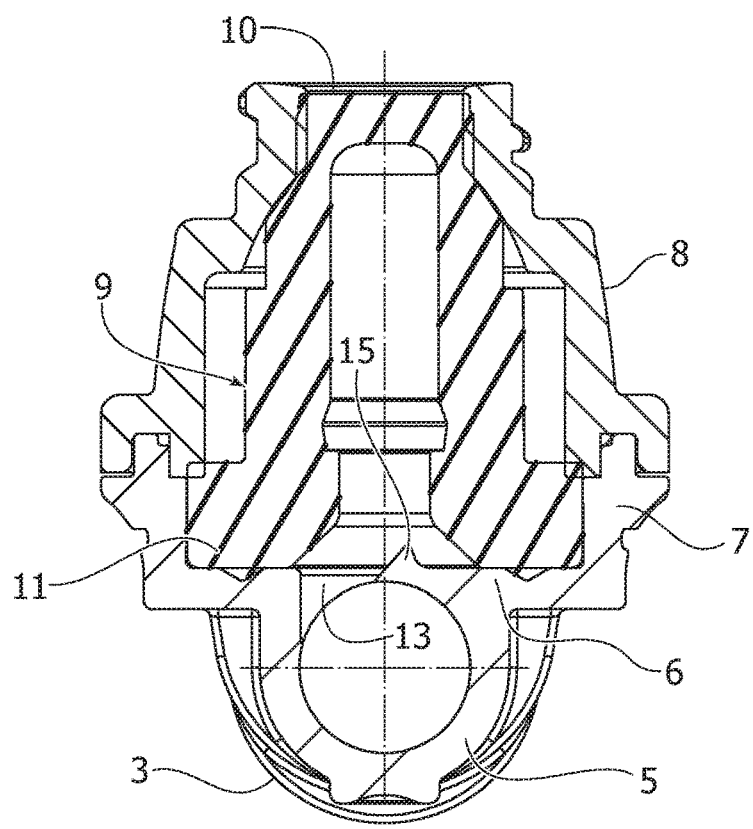
FIG. 5 is a cross-sectional view according to line V-V of FIG. 3.
Figure 6:
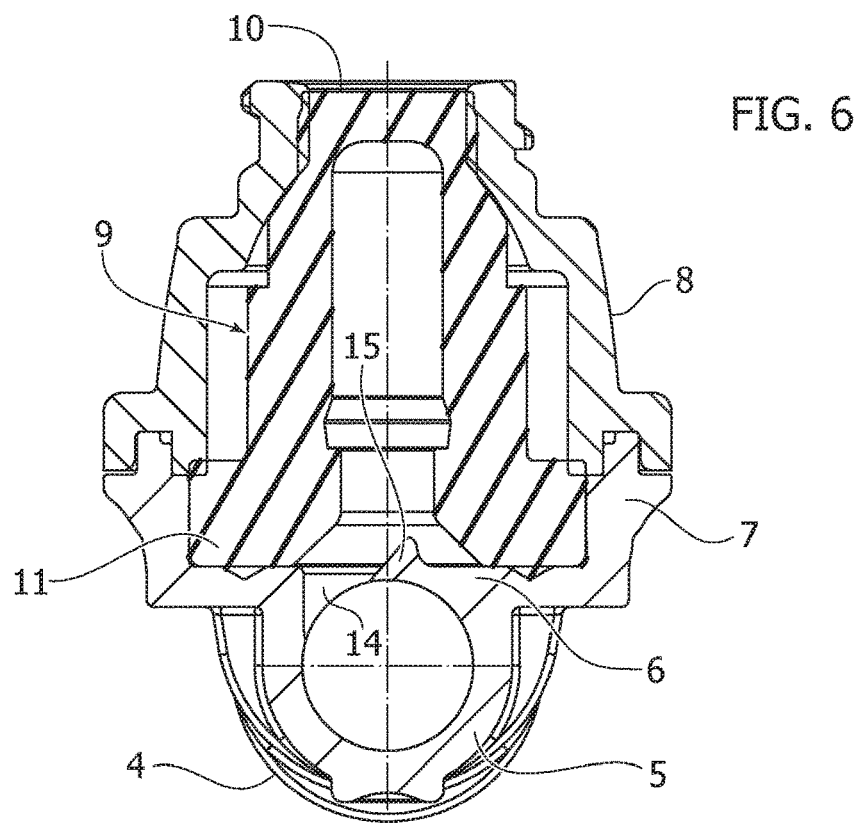
FIG. 6 is a cross-sectional view according to line VI-VI of FIG. 3.

With reference to the drawings, and in particular to FIGS. 1-3, the flow component for hemodialysis medical lines according to the invention essentially comprises a body made of moulded plastic material 1 that forms, in a single piece, a duct 2 having a first end tubular connector 3 and a second end tubular connector 4 coaxial to each other and interconnected by means of a small diameter portion 5 of the duct 2, according to a substantially converging-diverging configuration.

The end connectors 3 and 4 are designed to be connected, in use, to ducts respectively connected to a hemodialysis machine and to a patient subjected to hemodialysis.

At the small diameter portion 5, the body 1 forms a circular wall 6, represented in larger detail in FIGS. 7 and 8 to be addressed further hereinafter, surrounded by an annular flange 7.

An intermediate tubular connector 8, typically of the female luer lock type designed to be coupled with a complementary male luer lock connector, is sealingly fixed to such annular flange 7.

A hollow elastic element 9, typically made of elastomeric material, whose longitudinal axis is indicated with Z in FIG. 3 is arranged in the intermediate tubular connector 8. The hollow elastic element 9 has a distal end 10 normally arranged substantially flushed with respect to the free end of the intermediate tubular connector 8, and a proximal end 11 that forms a support base on the circular wall 6 of the body 1. The condition shown in the drawings (FIGS. 3-6) corresponds to the non-deformed configuration of the hollow elastic element 9 in which the intermediate tubular connector 8 is sealingly closed in proximity of the distal end 10, which is immediately accessible from outside so as to be cleaned and disinfected. Should the complementary male luer lock connector be used with the intermediate connector 8, the hollow elastic element 9 is partly deformed and compressed ("luer activated") so as to open the communication between the intermediate connector 8 and the duct 2.

The hollow elastic element 9 delimits, therein, an axially extended cavity 12, closed at the distal end 10 and in which, in use, a portion of blood flow flowing through the duct 2 between the end connectors 3 and 4 thereof can enter and exit through a pair of by-pass apertures 13, 14, addressed below, formed through the flat wall 6.

Figure 7:
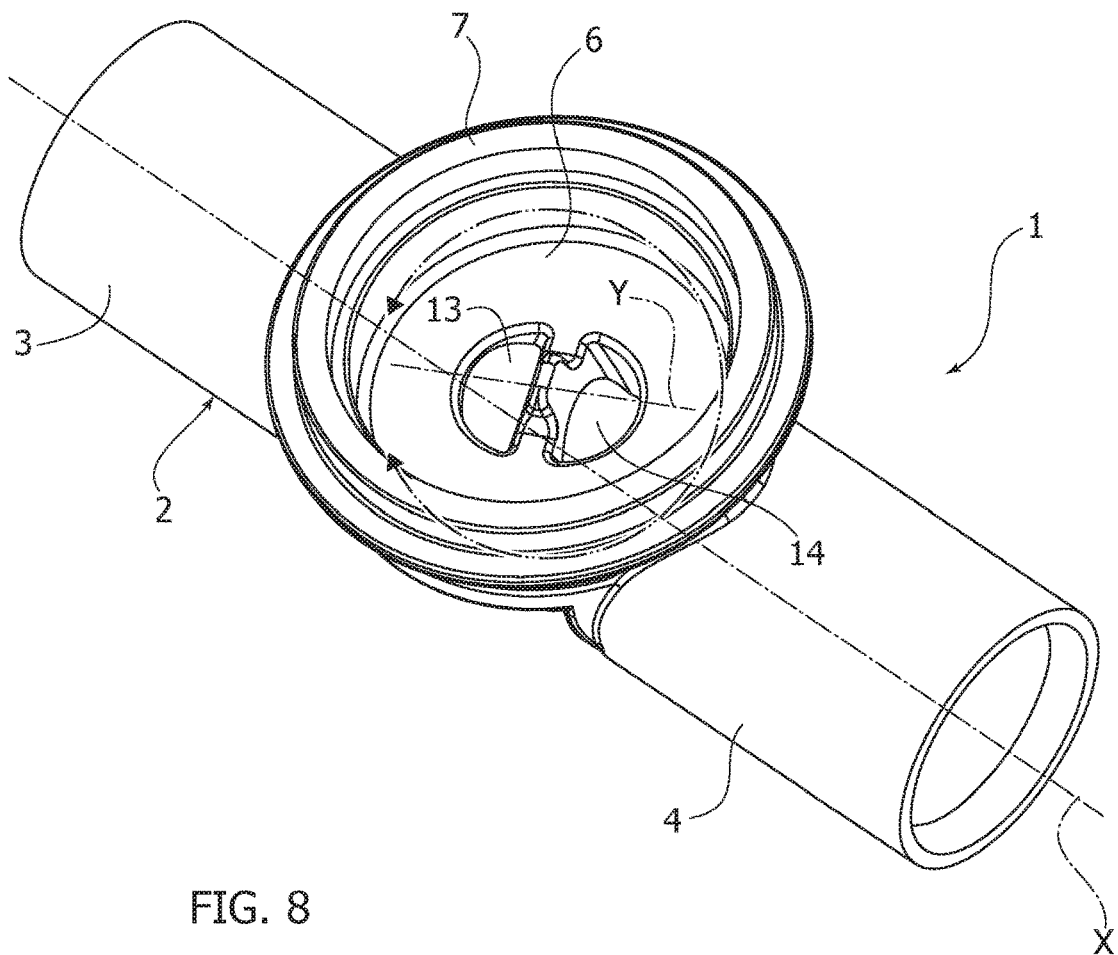
FIG. 7 is a perspective view of the body of the flow component from which the intermediate tubular connector was removed.
Figure 8:
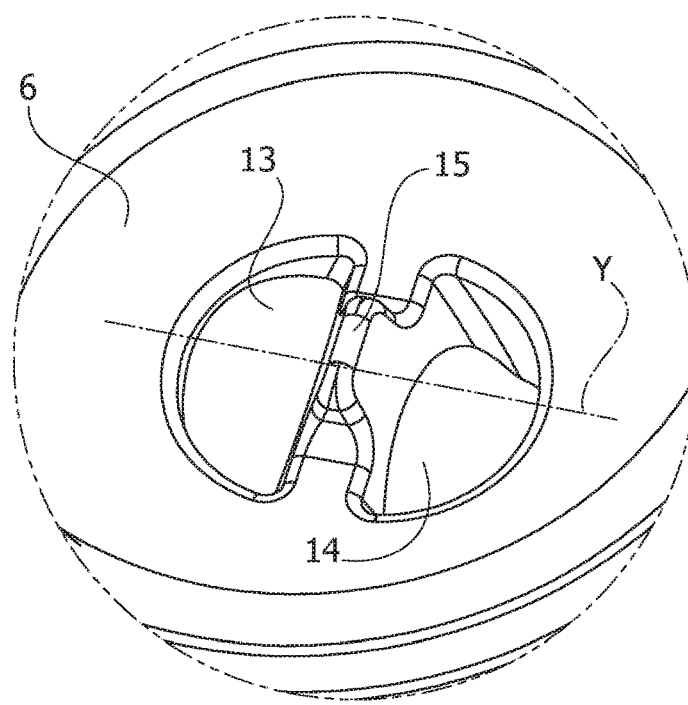
FIG. 8 shows an enlarged scale of a part of FIG. 7.

The by-pass apertures 13 and 14, represented further in detail in FIGS. 7 and 8, are arranged one upstream and the other downstream of the axis Z with respect to the direction of blood flow into the duct 2 and they are configured so that, in use, the blood flow that traverses the duct 2 and which—as mentioned—partly penetrates into the cavity 12 of the hollow elastic element 9, is diverted in a unique manner and subjected to a swirling motion along such cavity 12. This effect is attained thanks to the fact that the by-pass apertures 13 and 14 have a generally juxtaposed semi-circular shape and they are separated from each other by a baffle or diverter fin 15 projecting from the wall 6 towards the internal of the cavity 12. As clearly observable in FIG. 8, a plane or diametrical axis Y of the two apertures 13, 14 passing through the diverter fin 15 is arranged obliquely with respect to the longitudinal axis X of the duct 2. More precisely, the angle formed between the axis Y and the axis X is comprised between 10° and 50° and it is preferably in the order of about 45°.

The diverter fin 15 is also arranged obliquely with respect to the axis X of the duct 2 according to an angle comprised between 10° and 50° and preferably of the order of about 45°.

Thanks to this arrangement, the flow component according to the invention operates as follows.

Assuming that the blood flow traversing the duct 2 is directed by the end connector 3 towards the end connector 4, i.e. from left to right with reference to FIG. 3, during its path, part of the blood intercepts the upstream aperture 13, whose semi-circular and obliquely arranged shape widens towards one side with respect to such part of flow. Then, this part of the blood flow begins to be channelled into the smaller area of the aperture, and finds an increasingly wider aperture 13 as the flow advances progressively. Thus, the part of the blood flow is diverted and pushed with a spiral motion towards the internal of the cavity 12, in which it meets a depression due to the presence of the aperture 14 downstream. The blood cannot move directly towards the aperture 14, due to the presence of the diverter fin 15, but it is introduced along the cavity 12 with a generally helical swirling movement, before returning into the duct 2 through the aperture 14. Thus, the combination between the shape and orientation of the openings 13, 14 as well as the presence of the diverter fin 15 enables obtaining a spiral-like swirling flow that keeps the blood penetrated into the cavity 12 in motion, thus preventing stagnation and the ensuing deterioration thereof.

Obviously, the construction details and the embodiments may widely vary with respect to what has been described and illustrated, without departing from the scope of protection of the present invention as defined in the claims that follow.

The invention claimed is:

1. A flow component for hemodialysis medical lines, comprising:
    a duct having a first end tubular fitting and a second end tubular fitting coaxial to each other and designed to be connected to a line,
    said duct comprising an intermediate duct portion extending between and coaxial to said first end tubular fitting and said second end tubular fitting, said intermediate duct portion having a smaller diameter than said first end tubular fitting and said second end tubular fitting, said intermediate duct portion comprising an intermediate wall having inner surfaces bounding an open circular flow passage and an outer surface;
    an intermediate tubular connector of a female luer type arranged orthogonally to the duct between said first end tubular fitting and said second end tubular fitting and containing a valve device,
    wherein said valve device is formed by an elastic hollow element which normally keeps said intermediate tubular connector closed, said elastic hollow element elastically deformable following a coupling of the intermediate tubular connector with a complementary male luer connector, wherein said duct is internally configured so that, in use, a flow through said open circular flow passage is partially diverted towards the intermediate tubular connector and introduced with a swirling motion along a cavity of said elastic hollow element;

said intermediate wall extending between and connecting said first end tubular fitting and said second end tubular fitting, said intermediate wall comprising two juxtaposed by-pass apertures allowing flow through said intermediate wall and located respectively upstream and downstream of the elastic hollow element with respect to a flow within the duct;

said intermediate tubular connector delimited by said outer surface of said intermediate wall of said intermediate duct portion, said intermediate wall supporting the elastic hollow element;

said intermediate wall comprising an intermediate baffle between said by-pass apertures, said by-pass apertures being shaped and oriented so as to provide said swirling motion in combination with a separation of said by-pass apertures by said intermediate baffle, said intermediate baffle formed on said outer surface of said intermediate wall of said intermediate duct portion, and projecting into the cavity of said elastic hollow element from said outer surface of said intermediate wall, said outer surface of said intermediate wall located radially inwardly relative to radially outermost surfaces of said first end tubular fitting and said second end tubular fitting.

2. The flow component according to claim 1, wherein said by-pass apertures have a substantially juxtaposed semicircular shape and are oriented obliquely with respect to an axis of the duct.

3. The flow component according to claim 2, further comprising an aperture axis containing radiuses of said two by-pass apertures passing through said intermediate baffle that forms an angle comprised between 10° and 50° with respect to the axis of the duct.

4. The flow component according to claim 3 wherein the angle comprises about 45°.

5. The flow component according to claim 2, wherein said intermediate baffle forms an angle comprised between 10° and 50° with respect to the axis of the duct.

6. Flow component according to claim 1 wherein said intermediate baffle comprises a diverter fin having a distal tip opposite said intermediate wall, said intermediate wall surrounded by an annular flange connected to said intermediate tubular connector, said distal tip extending a distance from said intermediate wall less than said annular flange extends from said intermediate wall.

7. A flow component for hemodialysis medical lines, comprising:

a duct having a first end tubular fitting and a second end tubular fitting coaxial to each other and designed to be connected to a line, said duct comprising an intermediate duct portion extending between and coaxial to said first end tubular fitting and said second end tubular fitting, said intermediate duct portion having a smaller diameter than said first end tubular fitting and said second end tubular fitting, said intermediate duct portion comprising an intermediate wall having inner surfaces bounding an open circular flow passage and an outer surface;

an intermediate tubular connector of a female luer type comprising an elastic hollow element which normally keeps said intermediate tubular connector closed, said elastic hollow element elastically deformable following a coupling of the intermediate tubular connector with a complementary male luer connector;

said intermediate wall extending between and connecting said first end tubular fitting and said second end tubular fitting, said intermediate wall comprising two juxtaposed by-pass apertures allowing flow through said intermediate wall and located respectively upstream and downstream of the elastic hollow element with respect to a flow within the duct;

said outer surface of said intermediate wall of said intermediate duct portion supporting the elastic hollow element;

said intermediate wall comprising an intermediate baffle between said by-pass apertures, wherein a shape and orientation of said by-pass apertures in combination with a separation of said by-pass apertures by said intermediate baffle provide a swirling motion of a partially diverted flow diverted from said open circular flow passage toward said intermediate tubular connector; and said intermediate baffle formed on said outer surface of said intermediate wall of said intermediate duct portion and projecting into a cavity of said elastic hollow element from said outer surface of said intermediate wall, said outer surface of said intermediate wall located radially inwardly relative to radially outermost surfaces of said first end tubular fitting and said second end tubular fitting.

* * * * *